United States Patent [19]

Stucky et al.

[11] Patent Number: 5,446,160

[45] Date of Patent: Aug. 29, 1995

[54] PROCESS FOR PREPARING IMIDAZOPYRIDINE DERIVATIVES

[75] Inventors: Gerhard Stucky; René Imwinkelried, both of Brig-Glis, Switzerland

[73] Assignee: Lonza Ltd., Gampel/Valais, Switzerland

[21] Appl. No.: 308,448

[22] Filed: Sep. 19, 1994

[30] Foreign Application Priority Data

Sep. 17, 1993 [CH] Switzerland .................. 02 816/93-8

[51] Int. Cl.$^6$ ........................................... C07D 471/04
[52] U.S. Cl. .................................................... 546/118
[58] Field of Search ...................... 546/118; 548/326.5

[56] References Cited

U.S. PATENT DOCUMENTS

| | | |
|---|---|---|
| 5,066,654 | 11/1991 | Taylor, Jr. et al. ................. 514/256 |
| 5,240,938 | 8/1993 | Greenlee et al. ................... 514/303 |

FOREIGN PATENT DOCUMENTS

| | | |
|---|---|---|
| 0130461 | 1/1985 | European Pat. Off. . |
| 0385850 | 12/1990 | European Pat. Off. . |
| 0510813 | 10/1992 | European Pat. Off. . |

OTHER PUBLICATIONS

Katritsky and Rees, Comprehensive Heterocyclic Chem., Pergamon Press, vol. 5–part 4A, pp. 373, 374, 438, 439, 607 & 635–639 (1984).
J. Med. Chem., (1991), 34, pp. 2919–2922.
Brooker et al., J. Am., Chem. Soc., (1935), 57, pp. 2480–2488.
WO 93/23399 International Published Application, Nov. 1993.

*Primary Examiner*—Bernard Dentz
*Attorney, Agent, or Firm*—Fisher, Christen & Sabol

[57] ABSTRACT

A new process for preparing imidazopyridines of the general formula:

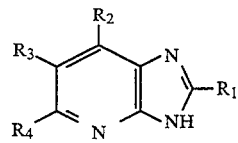

wherein $R_1$ is an alkyl, cycloalkyl, aryl or aralkyl group or is a heterocyclic radical, $R_2$ and $R_4$ are identical or different and are hydrogen, a hydroxy, a cyano, alkyl, cycloalkyl, aryl or aralkyl group or are an alkanoyl or an alkoxy-carbonyl group, and $R_3$ is hydrogen, an alkyl, aryl or aralkyl group or a halogen atom. In the key step of the process, an imidate of the formula:

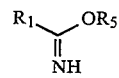

is cyclized with aminoacetonitrile and a 1,3-dicarbonyl compound of the general formula:

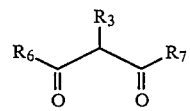

The imidazopyridines are valuable intermediates for the preparation of angiotensin II antagonists.

9 Claims, No Drawings

PROCESS FOR PREPARING IMIDAZOPYRIDINE DERIVATIVES

BACKGROUND OF THE INVENTION

1. Field of the Invention

The invention relates to a new process for preparing imidazopyridine derivatives of the general formula:

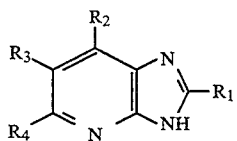
I wherein $R_1$ is an alkyl, cycloalkyl, aryl or aralkyl group or is a heterocyclic radical, $R_2$ and $R_4$ are identical or different and are hydrogen, a hydroxy, a cyano, alkyl, cycloalkyl, aryl or aralkyl group or are an alkanoyl or an alkoxy-carbonyl group, and $R_3$ is hydrogen, an alkyl, aryl or aralkyl group or a halogen atom.

2. Background Art

The literature reference *J. Med. Chem.*, (1991), 34, 2919–2922, describes how the above-described imidazopyridines can be obtained by reduction of 2-amino-3-nitropyridines and by subsequent condensation with an appropriate aliphatic carboxylic acid. However, the preparation of the starting materials for the 2-amino-3-nitropyridines is difficult, since the nitration of the corresponding aminopyridines does not proceed regioselectively.

BROAD DESCRIPTION OF THE INVENTION

An object of the invention is to provide a process which involves a simple route, which can be used on a large scale, to the desired imidazopyridines. Other objects and advantages of the invention are set out herein or are obvious herefrom to one ordinarily skilled in the art.

The objects and advantages of the invention are achieved by the process of the invention.

The invention involves a process for preparing imidazopyridine derivatives of the general formula:

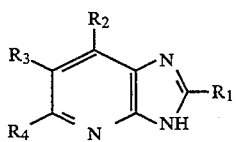
I wherein $R_1$ is an alkyl, cycloalkyl, aryl or aralkyl group or is a heterocyclic radical, $R_2$ and $R_4$ are identical or different and are hydrogen, a hydroxy, a cyano, alkyl, cycloalkyl, aryl or aralkyl group or are an alkanoyl or an alkoxy-carbonyl group, and $R_3$ is hydrogen, an alkyl, aryl or aralkyl group or a halogen atom. The process includes cyclizing an imidate of the general formula:

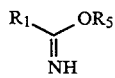
II wherein $R_1$ is as defined above and $R_5$ is alkyl, aryl or aralkyl, with aminoacetonitrile and a 1,3-dicarbonyl compound of the general formula:

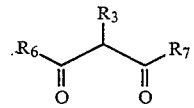
III wherein $R_3$ is as defined above and $R_6$ and $R_7$ are identical or different and are hydrogen, alkyl, aryl, aralkyl, alkoxy or alkoxycarbonyl, to give the final product of the general formula I.

Preferably the aminoacetonitrile is liberated from a salt of aminoacetonitrile by means of a base. Preferably the cyclization is carried out at a temperature between room temperature and the reflux temperature of the reaction mixture and in the presence or absence of an additional solvent. Preferably the imidate of the general formula II is obtained by reaction of a nitrile of the general formula:

$$R_1OH \qquad\qquad IV$$

wherein $R_1$ is as defined above, with an alcohol of the general formula:

$$R_5OH \qquad\qquad V$$

wherein $R_5$ is as defined above, in the presence of a hydrogen halide.

The compounds are used as intermediates for the preparation of angiotensin II antagonists. [*J. Med. Chem.*, (1991), 34, 2919 to 2922]

DETAILED DESCRIPTION OF THE INVENTION

The terms used for the individual radicals $R_1$ to $R_7$ have the following meanings.

The term alkyl group means a straight-chain or branched alkyl group having advantageously from 1 to 6 carbon atoms, preferably having from 1 to 4 carbon atoms. Examples of the alkyl group are methyl, ethyl, n-propyl, i-propyl, n-butyl and t-butyl group. The term cycloalkyl group advantageously means a $C-C_6$-cycloalkyl group, such as, cyclopropyl, cyclobutyl, cyclopentyl or cyclohexyl. The term aryl includes carbocyclic aromatics, advantageously phenyl or naphthyl. The term aralkyl means an aryl-substituted alkyl group, advantageously a phenyl-substituted $C_1$–$C_6$-alkyl group, in particular benzyl. The term alkanoyl group advantageously means a $(C_1$–$C_6)$-alkanoyl group, preferably acetyl. The term alkoxy advantageously means a $(C_1$–$C_6)$-alkoxy group, preferably methoxy or ethoxy.

The term heterocyclic radical advantageously means a heterocycle having a 5-membered or 6-membered ring and having nitrogen and/or oxygen and/or sulfur as the heteroatom. Likewise, the specified term includes condensed ring systems of heterocycles with one another or of heterocycles with carbocyclic systems. Examples of heterocycles having a 5-membered ring are the furans, the thiophenes, the pyrroles, the indoles, the pyrazoles, the imidazoles, the oxazoles, isoxazoles, the thiazoles, and the triazoles. Examples of heterocycles having a 6-membered ring are the pyridines, the quinolines, the isoquinolines, the acridines, the pyridazines, the pyrimidines, the pyrazines, the phenazines, the purines, and the pteridines.

Halogen is fluorine, chlorine, bromine or iodine; the preferred halogen is chlorine.

The specified groups, in particular the cyclic radicals, can in each case be monosubstituted or polysubstituted. Suitable radicals are, for example, halo, nitro, amino, alkylamino, dialkylamino, hydroxy, alkoxy, alkyl or alkanoyl. The above explanations of term meanings apply to these radicals.

The starting material of the process of the invention, the imidate of the general formula:

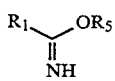     II wherein $R_1$ is as defined above and $R_5$ is alkyl, aryl or aralkyl, can be prepared by the method of Brooker et al., *J. Am Chem. Soc.*, (1935), 57, 2480ff, by reaction of a nitrile of the general formula:

     IV with an alcohol of the general formula:

     V wherein $R_5$ is as defined above, in the presence of a hydrogen halide to give an imidate hydrohalide, and subsequently liberating the imidate using a base. The nitrile of the general formula IV which is used is advantageously acetonitrile, propionitrile, butyronitrile or valeronitrile. Suitable aliphatic alcohols of the general formula V are methanol, ethanol, n- or i-propanol, n-, i- or t-butanol, preferably methanol. The preferred hydrogen halide is hydrogen chloride. The alcohol $R_5OH$ used can function as the solvent. However, an additional inert solvent, such as, an ether such as dioxane or diethyl ether or an aromatic hydrocarbon such as toluene, can be used.

The resultant imidate of the general formula II can be isolated from the reaction mixture in a manner known to those skilled in the art; it is advantageously fed to the subsequent stage dissolved in one of the specified solvent.

According to the invention, in the subsequent stage the imidate of the general formula II is cyclized with aminoacetonitrile and a 1,3-dicarbonyl compound of the general formula:

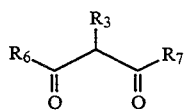     III wherein $R_3$ is as defined above and $R_6$ and $R_7$ are identical or different and are hydrogen or alkyl, aryl, aralkyl, alkoxy or alkoxycarbonyl, to give the final product.

Suitable 1,3-dicarbonyl compounds, where $R_6$ and $R_7$ are alkyl, are the alkanediones, such as, 2,4-pentanedione (acetylacetone), 3,5-heptanedione, 4,6-nonanedione or, where $R_3$ is methyl, 3-methyl-2,4-pentanedione (2-methylacetylacetone). Representatives where $R_6$ is alkyl and $R_7$ is alkoxy are the alkanoylacetic esters, such as, methyl acetoacetate or ethyl acetoacetate. The malonic esters, where $R_6$ and $R_7$ are alkoxy, are also advantageously used; examples are methyl malonate and ethyl malonate. Suitable compounds of the general formula III, where $R_6$ and $R_7$ are hydrogen, are malondialdehyde or the 2-substituted malondialdehydes. Further suitable representatives of the general formula III, where $R_6$ and $R_7$ are alkoxycarbonyl, are dimethyl 2,4-dioxopentanedioate or diethyl 2,4-dioxopentanedioate having $R_6$ and $R_7$ being methoxycarbonyl and ethoxycarbonyl.

The aminoacetonitrile can, in each case, be liberated directly prior to the reaction from a corresponding aminoaceonitrile salt, such as, the hydrochloride or the hydrosulfate by reacting it with a base, for example, ammonia. However, the aminoacetonitrile salt can also be added during the course of the reaction, for example in the form of a suspension, together with a base. The base used can be, for example, an alkali metal alkoxide, such as, sodium or potassium ethoxide, sodium/potassium methoxide or potassium t-butoxide in the corresponding alcohol, a trialkylamine, such as, triethylamine or ethyldiisopropylamine, an alkali metal hydroxide, such as NaOH or KOH in an aliphataic alcohol or water, or else alkali metal or alkaline earth metal hydrogen carbonates in water.

If desired, the 1,3-dicarbonyl compound can function as the solvent, so that an additional solvent is in principle not necessary. Selection of solvent, where applicable, is not especially critical. Good results can be obtained using lower aliphataic alcohols, such as, methanol or ethanol, halogenated hydrocarbons, such as, methylene chloride, ethers, such as, dioxane, or using aromatic hydrocarbons such as, toluene or xylene.

The reaction is advantageously carried out between room temperature and the reflux temperature of the respective solvent, preferably between 50° C. and the reflux temperature of the solvent.

After the reaction is complete, the imidazopyridine can be separated off from the reaction mixture in a conventional manner.

EXAMPLE 1

(a) Process for preparing methyl propionimidate 220 g of HCl (6 mol) was passed at 0° C. into a solution of 220 g (4 mol) of propionitrile and 128.4 g (4 mol) of methanol in 400 ml of diethyl ether. After addition was complete, the reaction mixture was stirred for a further 16 hours at 0° C. The crystalline solid was filtered off and washed twice with ether. After drying in a high vacuum, there remained 460 g (93 percent) of the title product as hydrochloride. Other data concerning the HCl product was:

$^1$H-NMR (DMSO, 300 MHz) δ1.15 (t, 3H) 2.71 (q, 2H) 4.1 (s, 3H) 11.2 (broad s, 1H) 12.2 (broad s, 1H)

To liberate the title product, the reaction mixture was poured into 2N $K_2CO_3$ solution. After phase separation and distilling off the ether, the free imidate remained as a colorless liquid. The free product had a boiling point of 88° to 92° C. Other data concerning the free product was:

$^1$H-NMR (CD$_3$OD, 400 MHz) δ1.1 (t, 3H) 2.3 (q, 2H) 3.65 (s, 3H) 4.85 (s, 1H)

(b) Process for preparing 2-ethyl-5,7-dimethyl-3H-imidazo[4,5-b]pyridine

A solution of 4.36 g (50 mmol) of the product from 1(a) and 50 g (500 mmol; 10 eq) of acetyl acetone in 50 ml of toluene was heated to 70° C. and admixed with a filtered solution of 4.72 g (50 mmol) of aminoacetonitrile hydrochloride and 2 g (50 mmol) of NaOH in 30 ml of methanol. The mixture was stirred for 4 hours at 70° C. and subsequently slowly heated to 110° C., with the methanol and water being distilled off. After a further hour at the reflux temperature, the mixture was allowed to cool to room temperature and the solvent was evaporated on a rotary evaporator. The solid residue was dissolved in a little hot ethyl acetate, filtered hot and subsequently cooled again to room temperature. The solid which crystallized out was filtered off, washed with a little cold ethyl acetate and dried in vacuo. This gave 4.61 g (52 percent) of pale yellow title product. The product had a melting point of 148.8° to 150.4° C. Other data concerning the product was:

$^1$H-NMR (CD$_3$OD, 400 MHz) δ1.4 (t, 3H) 2.55 (s, 6H) 2.9 (q, 2H) 6.9 (s, 1H)

EXAMPLE 2

Process for preparing
2-ethyl-5,6,7-trimethyl-3H-imidazo[4,5-b]pyuridine

A solution of 13.3 g (0.15 mol) of methyl propionimidate [product from Example 1(a)] and 33.57 g (0.285 mol) of 3-methyl-2,4-pentanedione in 150 ml of toluene was heated to 65° C. and admixed with a suspension of 13.9 g (0.15 mol) of aminoacetonitrile hydrochloride and 6 g (0.15 mol) of NaOH in 80 ml of methanol. The mixture was stirred for 2 hours at 65° to 70° C. and the methanol was subsequently distilled off. The mixture was cooled to room temperature, admixed with 50 ml of water and the pH adjusted to 1.3 using conc. HCl. The phases were separated and the aqueous phase was again brought to pH 8.4 using NaOH solution. The aqueous phase was extracted a number of times with ethyl acetate, the combined organic phase was dried over MgSO$_4$ and evaporated on a rotary evaporator. The crude product was purified by recrystallization from acetone. This gave 3.75 g (13 percent) of pure product. The product had a melting point of 183.5° to 184.4° C. Other data concerning the product was:

$^1$H-NMR (CDCl$_3$, 300 MHz): δ1.45 (t, 3H) 2.3 (s, 3H) 2.63 (s, 3H) 2.68 (s, 3H) 3.05 (q, 2H) 12.7–13.1 (br, 1H)

EXAMPLE 3

Process for preparing
2-cyclopropyl-5,7-dimethyl-3H-imidazo[4,5,b]pyridine 36.0 g (0.2 mol) of sodium methoxide (30 percent strength solution in methanol) was slowly added dropwise at 0° C. to a solution of 30.13 (0.2 mol) of methyl cyclopropylimidate hydrochloride in 20 ml of methanol. The mixture obtained was subsequently admixed at the same temperature with 100.1 g (1 mol) of acetylacetone and then heated to 50° C. To the resulting suspension was added a suspension of 18.5 g (0.2 mol) of aminoacetonitrile hydrochloride and 8 g (0.2 mol) of NaOH in 50 ml of methanol. The mixture was stirred for 16 hours at 65° to 70° C. and subsequently the methanol was distilled off. The temperature gradually rose to 110° C. The mixture was left for a further 3 hours at this temperature and subsequently cooled to room temperature. 150 ml of water was added, the pH adjsted to 1.3 using conc. HCl and the mixture was subsequently neutralized again using NaOH. The product was extracted a number of times with ethyl acetate, the combined organic phase was dried over MgSO$_4$ and evaporated on a rotary evaporator. The crude product was taken up in 200 ml of ether, stirred and subsequently filtered again. The residual solid was slurried into 200 ml of water and filtered again after 4 hours. 17.75 g of product was obtained. This was recrystallized from toluene, giving 15.3 g (41 percent) of pure product as yellowish crystals. The product had a melting point of 171.7° to 172.6° C. Other data concerning the product was:

$^1$H-NMR (CD$_3$OD, 300 MHz): δ1.1–1.3 (m, 4H) 2.1–2.25 (m, 1H) 2.5 (s, 3H) 2.55 ( s, 3H) 6.9 (s, 1H)

EXAMPLE 4

Process for preparing
2-ethyl-5-methyl-7-phenyl-3H-imidazo [4,5-b]pyridine
and
2-ethyl-7-methyl-5-phenyl-3H-imidazo[4,5-b]pyridine A solution of 3.6 g (40 mmol) of methyl propinimidate [product from Example 1(a)] and 14.6 g (90 mmol) of benzoylacetone in 50 ml of xylene was heated to 70° C. and admixed with a suspension of 3.7 g (40 mmol) of aminoacetonitrile hydrochloride and 1.6 g (40 mmol) of NaOH in 40 ml of methanol. The mixture was stirred for 4 hours at 65° to 70° C. and the methanol was subsequently distilled off. The temperature gradually rose to 130° C. The mixture was cooled to room temperature, admixed with 150 ml of water and the pH adjusted to 2.2 using conc. HCl. 100 ml of ethyl acetate was added, the phases were separated and the aqueous phase was again brought to pH 7.2 using NaOH solution. The aqueous phase was extracted a number of times with ethyl acetate, the combined organic phase was dried over MgSO$_4$ and evaporated on a rotary evaporator. This gave 5.05 g of crude product which contained the isomeric title compounds in a ratio of about 4:1 (according to the $^1$H-NMR spectrum). The 5-methyl-7-phenyl derivative was isolated as the main isomer by column chromatography (ethyl acetate/hexane 5:1). This gave 0.73 g as the main fraction, and also 1.26 g of a mixed fraction. The product had a melting point of 187.4° to 190.4° C. Other data concerning the product was:

$^1$H-NMR (DMSO, 400 MHz) (of the 5-methyl-7-phenyl isomer): δ1.4 ( t, 3H) 2.6 (s, 3H) 2.7 (q, 2H) 7.34–7.52 (m, 3H) 7.6 (s, 1H) 8.06–8.12 (m, 2H)

What is claimed is:

1. A process for preparing an imidazopyridine derivative of the formula:

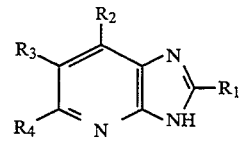

wherein R$_1$ is an alkyl, cycloalkyl, aryl or aralkyl group or is a heterocyclic radical, R$_2$ and R$_4$ are identical or different and are hydrogen, a hydroxy, a cyano, alkyl, cycloalkyl, aryl or aralkyl group or are an alkanoyl or an alkoxy-carbonyl group, and R$_3$ is hydrogen, an alkyl, aryl or aralkyl group or a halogen atom, comprising cyclizing an imidate of the formula:

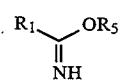

wherein R$_1$ is as defined above and R$_5$ is alkyl, aryl or aralkyl, with aminoacetonitrile and a 1,3-dicarbonyl compound of the formula:

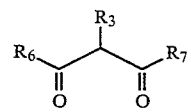

wherein $R_3$ is as defined above, and $R_6$ and $R_7$ are identical or different and are hydrogen, cyano, cycloalkyl, alkanoyl, alkyl, aryl, aralkyl, alkoxy or alkoxycarbonyl, to give the imidazopyridine derivative of the formula I.

2. The process according to claim 1 wherein the aminoacetonitrile is liberated from a salt of aminoacetonitrile by means of a base.

3. The process according to claim 2 wherein the cyclization is carried out at a temperature between room temperature and the reflux temperature of the reaction mixture.

4. The process according to claim 3 wherein the cyclization is conducted in the presence of an additional solvent.

5. The process according to claim 3 wherein the cyclization is conducted in the absence of an additional solvent.

6. The process according to claim 1 wherein the imidate of the formula II is obtained by reaction of a nitrile of the formula:

$$R_1CN \qquad \qquad IV$$

wherein $R_1$ is as defined above, with an alcohol of the formula:

$$R_5OH \qquad \qquad V$$

wherein $R_5$ is as defined above, in the presence of a hydrogen halide.

7. The process according to claim 1 wherein the cyclization is carried out at a temperature between room temperature and the reflux temperature of the reaction mixture.

8. The process according to claim 7 wherein the cyclization is conducted in the presence of an additional solvent.

9. The process according to claim 7 wherein the cyclization is conducted in the absence of an additional solvent.

* * * * *